(12) United States Patent
Dittmer et al.

(10) Patent No.: US 9,557,328 B2
(45) Date of Patent: Jan. 31, 2017

(54) MAGNETIC SENSOR DEVICE, METHOD OF OPERATING SUCH A DEVICE AND SAMPLE

(75) Inventors: Wendy Uyen Dittmer, Eindhoven (NL); Femke Karina De Theije, Berghem (NL); Albert Hendrik Jan Immink, Eindhoven (NL); Jeroen Hans Nieuwenhuis, Waalre (NL); Petrus Johannes Wilhelmus Van Lankvelt, Boekel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 13/381,115

(22) PCT Filed: Jun. 24, 2010

(86) PCT No.: PCT/IB2010/052880
§ 371 (c)(1),
(2), (4) Date: Dec. 28, 2011

(87) PCT Pub. No.: WO2011/001337
PCT Pub. Date: Jan. 6, 2011

(65) Prior Publication Data
US 2012/0107961 A1    May 3, 2012

(30) Foreign Application Priority Data
Jun. 30, 2009 (EP) .................... 09164234

(51) Int. Cl.
*G01N 33/543* (2006.01)
*G01N 27/74* (2006.01)
*G01N 21/552* (2014.01)

(52) U.S. Cl.
CPC ...... *G01N 33/54326* (2013.01); *G01N 27/745* (2013.01); *G01N 33/54366* (2013.01); *G01N 33/54386* (2013.01); *G01N 21/552* (2013.01)

(58) Field of Classification Search
CPC ............ C12Q 1/6816; C12Q 2545/101; C12Q 2563/103; C12Q 2563/143; C12Q 2537/125; C12Q 2545/114; C12Q 2563/107; C12Q 2565/50; G01N 33/54313; G01N 33/585; G01N 33/582; G01N 33/54326
(Continued)

(56) References Cited

U.S. PATENT DOCUMENTS 5,679,526 A * 10/1997 Buechler et al. ............. 436/518
5,856,203 A    1/1999 Robinson et al.
(Continued)

FOREIGN PATENT DOCUMENTS

CN    1608206 A    4/2005
CN    101258407 A    9/2008
(Continued)

OTHER PUBLICATIONS

J. Kiely et al, "Paramagnetic particle detection for use with an immunoassay based biosensor", IET Sci. Meas. Technol, 2007, 1, (5), pp. 270-275.
(Continued)

*Primary Examiner* — Rebecca Martinez (57) ABSTRACT

A sensor device (1) for detecting the presence of a target molecule (20) in a sample, is disclosed. The sensor device comprises a measurement sensor (2) comprising a first moiety (16) for forming a binding couple with a first further moiety comprising the target molecule (20) and a detectable label (40) and a reference sensor (3) comprising a second moiety (50) for forming a further binding couple with a second further moiety comprising a further detectable label (40'). The sensor device is adapted to generate a first detection signal (14) from the detection of the detectable label (40) in the first further moiety bound to the first moiety
(Continued)

(16) and to generate a second detection signal (14') from the detection of the further detectable label (40') in the second further moiety bound to the second moiety (50), wherein at least during operation of the sensor device the second further moiety is expected to be present in a predefined amount such that the value of the second detection signal (14') falls within an expected signal value window when the binding reaction of the second further moiety to the second moiety takes place as expected. An apparatus comprising such a sensor device, methods of operating the sensor device and apparatus and a sample for use with the sensor device are also disclosed.

12 Claims, 5 Drawing Sheets

(58) Field of Classification Search
 USPC .................................................. 436/525, 526
 See application file for complete search history.

(56) References Cited

U.S. PATENT DOCUMENTS

| | | | | |
|---|---|---|---|---|
| 5,939,272 | A * | 8/1999 | Buechler | G01N 33/53 435/7.1 |
| 5,981,297 | A | 11/1999 | Baselt | |
| 6,696,304 | B1 * | 2/2004 | Davies | 436/518 |
| 2006/0160164 | A1 * | 7/2006 | Miller et al. | 435/7.93 |
| 2007/0020700 | A1 * | 1/2007 | Carpenter et al. | 435/7.5 |
| 2008/0200788 | A1 * | 8/2008 | Brister et al. | 600/345 |

FOREIGN PATENT DOCUMENTS

| | | |
|---|---|---|
| EP | 1645880 A1 | 4/2006 |
| JP | 2000236877 A | 9/2000 |
| JP | 2007107920 A | 4/2007 |
| JP | 2008P072156 A | 3/2008 |
| WO | 03054523 A2 | 7/2003 |
| WO | 03056296 A2 | 7/2003 |
| WO | 2005026689 A2 | 3/2005 |
| WO | 2007029192 A1 | 3/2007 |
| WO | 2007060601 A1 | 5/2007 |
| WO | 2008044214 A1 | 4/2008 |
| WO | 2008072156 A2 | 6/2008 |
| WO | 2009057024 A1 | 5/2009 |
| WO | 2009072045 A1 | 6/2009 |

OTHER PUBLICATIONS

Paek, Se-Hwan et al "Irreversible Enzyme-Shuttle Immunoassay" Biotechnology and Bioengineering, Mar. 25, 1992, vol. 39, No. 7. pp. 753-764.

Graf, E. et al "Reverse Hybridization on a Microplate: A Rapid Method for the Identification of Dairy Microorganisms" Milchwissenschaft, VV GMBH Volkswirtschaftlicher Verlag, vol. 53, No. 9, Jan. 1, 1998. pp. 494-498.

* cited by examiner

MAGNETIC SENSOR DEVICE, METHOD OF OPERATING SUCH A DEVICE AND SAMPLE

FIELD OF THE INVENTION

The present invention relates to a sensor device for detecting the presence of a target molecule in a sample, comprising a measurement surface region carrying a first moiety for selectively binding a first further moiety comprising the target molecule and a detectable label and being adapted to generate a first detection signal from the detectable label of the further moiety bound to the first moiety.

The present invention further relates to an apparatus comprising such a sensor device.

The present invention yet further relates to a method of operating such a sensor device.

The present invention even further relates to a sample for use with such a sensor device.

BACKGROUND OF THE INVENTION

In the field of medial diagnostics, assay-based sensor devices are rapidly gaining popularity because of the prospect of being able to accurately determine the presence and concentration of a wide variety of analytes in samples of interest. To this end, the analyte is attached to a detectable label such a fluorescent or chemoluminescent probe, an enzyme for converting a calorimetric substrate or a magnetic particle. Either the analyte or a further entity attached to the detectable label forms a selective bond, i.e. a highly specific binding with e.g. an antibody attached to a sensor area of the sensor device such that the concentration of the analyte can be detected from the presence of the detectable label in the sensor area upon the formation of the highly specific binding, for instance by exposing a fluorescent probe to electromagnetic radiation having a suitable wavelength for electronically exciting the probe or by exposing a chemoluminescent probe to an appropriate catalyst (e.g. heat) to initiate the chemoluminescent reaction and measuring the intensity of the emitted light in both instances or by placing the magnetic particles in an (electro)magnetic field and measuring the interaction of the particles with this field. For instance, the particles may be placed in a light beam where the amount of scattering of the light beam caused by the interaction with the magnetic particles can be quantified by measuring the intensity of the reflected light beam.

Many suitable specific binding pair candidates such as strong binding couples are known, which are typically based on a lock-and-key type interaction between a receptor molecule and a molecule, e.g. a drug. This makes assay-based sensor devices particularly suitable to determine the presence or absence of specific proteins and other biological compounds such as DNA, RNA, hormones, metabolites, drugs and so on, or to determine the activity and function of active and catalytic biomolecules such as proteins, peptides, prions, enzymes, aptamers, ribozymes and deoxyribozymes. For instance, immunoassays are already used to determine the specific amount of specific proteins in body fluids to aid further diagnosis and treatment.

Several different types of assays exist. An example of an immunoassay is the enzyme-linked immunosorbent assay (ELISA), in which two antibodies are used that bind two separate, non-overlapping epitopes on the antigen. This may be accomplished by using two monoclonal antibodies that selective bind to different discrete sites or by using affinity-purified polyclonal antibodies that have been raised to different epitopes on the antigen. One of the antibodies is bound to the sensor surface whereas the other antibody is labeled with an enzyme. The antigen concentration can be determined following a binding reaction and the rinsing of the binding site to wash away unbound material by measuring the amount of colorimetric substrate converted by the enzyme label attached to the second antibody. Due to the requirement of two antibodies, such assays are commonly referred to sandwich assays because the analyte of interest is sandwiched between these two different antibodies.

The competitive assay is another example of an immunoassay. Here, an epitope of the target molecule competes with a homologue expected to have a similar epitope to bind to a paratope on either a detectable label or a sensor surface. In the first case, the homologue is attached to the sensor surface. In the latter case, the homologue is attached to the detectable label. The concentration of the target molecule is determined indirectly from the detected label concentration on the binding site. Such assays are particularly useful for the detection of target molecules having a single epitope only, such that these target molecules cannot be detected using sandwich assays. Further examples of known assays can for instance be found in WO 2007/060601, and other examples will be apparent to the skilled person.

Assay-based sensors provide promising new opportunities in the field of medical diagnostics. Sensor devices utilizing the presence of a magnetic label on a biomolecule are of particular interest, for instance because the application of a magnetic field can accelerate the formation of the highly specific binding on the measurement site such that the binding reaction can be completed in a short time span, which opens up the possibility of offering assay-based sensor devices for diagnostic purposes to untrained staff, non-technical personnel, directly to the patient, and so on without the need for the presence of a medical professional.

As is the case with any type of assay-based device, misuse of the device can produce unreliable diagnostic results. For instance, the biomolecules that are attached to the sensor surface as the first part of the binding couple can degrade when the sensor device is exposed to adverse environmental conditions or has been otherwise damaged. Also, the correct procedure for preparing the sample and/or applying the sample may not be followed, e.g. the sample is incorrectly prepared, the wrong amount of sample is added and so on, which also can cause erroneous measurement signals.

Regulatory requirements dictate that for the distribution of some medical devices in such application domains, fail-safe mechanisms are present in the device for instance to indicate to a user that the device has become unreliable. For instance, CLIA waived regulatory approval is preferred for tests to diagnose e.g. heart attacks because this allows untrained operators of the medical device to perform the test. This approval is conditional on the presence of such fail-safe mechanisms. The presence of such fail-safe mechanisms is equally of crucial importance in other emergency situations where the sensor device is used for making clinical decisions. Hence, there exists a need to be able to predict the accuracy of a diagnostic result obtained with an assay-based sensor device.

SUMMARY OF THE INVENTION

The present invention seeks to provide a sensor device for detecting the presence of a target molecule in a sample in which a fail-safe mechanism has been included.

The present invention further seeks to provide an apparatus comprises such a sensor device.

The present invention yet further seeks to provide a method of operating such a sensor device.

The present invention yet further seeks to provide a method of determining the accuracy of a measurement signal generated by such a sensor device.

The present invention yet further seeks to provide a sample for use with such a sensor device.

According to a first aspect, there is provided a sensor device for detecting the presence of a target molecule in a stationary sample, comprising a measurement surface region carrying a first moiety for selectively binding to a first further moiety comprising a detectable label, the amount of the first further moiety binding to the first moiety being related to the amount of the target molecule present in said sample; and a reference surface region carrying a second moiety for selectively binding to a second further moiety comprising a further detectable label, said sensor device being adapted to generate a first detection signal from the detection of the detectable label in the first further moiety bound to the first moiety; and generate a second detection signal from the detection of the further detectable label in the second further moiety bound to the second moiety, wherein at least during operation of the sensor device the second further moiety is expected to be present in a predefined amount such that the value of the second detection signal falls within an expected signal value window when the binding reaction of the second further moiety to the second moiety takes place as expected.

The present invention is based on the realization that in sensor devices comprising an assay for the detection of the presence of a target molecule in a stationary sample, i.e. a sample that does not flow over the sensor area during the detection measurement, the accuracy of the detection signal corresponding to the amount of target molecule bound to the measurement binding site or the amount of target molecule inhibiting the binding of the labeled particle to the measurement binding site can be verified by the generation of a second detection signal from a further assay expected to bind a further target that is expected to be present in a known quantity during the generation of the second detection signal.

Consequently, the second detection signal will have a known expectation value, to which the actual value of the second detection signal can be compared. This can for instance be used to check if second detection signal value falls within acceptable limits. This facilitates the detection of a wide range of failures. For instance, in case the first moiety and second moiety have comparable stability characteristics, which is usually the case when using biomolecules as the parts of the respective binding couples that are attached to the sensor surface, the deviation of the second detection signal from its expectation value in this case indicates that the binding sites at the sensor surface are no longer reliable. Also, the incorrect preparation or administration of a sample will lead to a deviation of the second measurement signal from its expectation value for instance because of the presence of the wrong labeled moiety, the omission of the labeled moiety from the sample or the administration of incorrect amount of sample.

Other errors that can be detected include the premature termination of the binding reaction and irregularities in the binding reaction between epitope and paratope. Such errors can be derived from a deviation from the time-dependent expectation value of the second detection signal during the binding reaction thus utilizing the fact that binding couples tend to have stable, i.e. reproducible, reaction constants.

In an embodiment, the detectable label and the further detectable label are the same, and wherein the first further moiety comprises the target molecule and the second further moiety. In this embodiment, the measurement surface region may form part of a sandwich assay for binding the target molecule. The second further moiety may comprise a secondary antibody for completing the sandwich assay. In this embodiment, care has to be taken that the second further moiety is present in sufficient excess during use of the sensor device to ensure that the binding reaction rates between the second further moiety and the target molecule and the second moiety and the second further moiety at the reference surface region are not limited by the availability of the second further moiety.

In an alternative embodiment, the first further moiety has no significant affinity for the second moiety and the second further moiety has no significant affinity for the first moiety. This has the advantage that no excess amounts of the second further moiety are required to be present because the binding reactions on the respective sensor sites are not influenced by the moieties intended to bind on the other sensor site. Many selective binding reactants including strong binding couple combinations or other suitable selective binding pairs may be used for the measurement sensor and the reference sensor. Preferably, the highly specific binding pair is selected from the group of hapten-antibody pairs such as biotin-antibiotin, fluorescinisothiocyanate-anti fluorescinisothiocyanate and Texas Red-antiTexas Red; antibody-antiantibody pairs and small molecule-protein pairs such as avidin-biotin although other types of specific or selective binding combinations may also be suitable.

The measurement surface region may be located in a first measurement chamber and the reference surface region may be located in a second measurement chamber. This has the advantage that any adverse interaction of the second further moiety with the measurement assay is avoided. Alternatively, the measurement surface region and the reference surface region may be located in the same measurement chamber, which has the advantage that both regions are exposed to the sample at the same time, such that the sample conditions for the reference measurement and the target measurement are the same, thus improving the robustness of the failure assessment.

In an embodiment, the second further moiety is present in the sensor device in a dried form. This has the advantage that the amount of the further moiety that is present during the reference measurement can be accurately controlled, thus reducing the risk of the sensor device being incorrectly rejected because of the addition of the incorrect amount of the second further moiety to a sample. Alternatively, a known amount of the further second moiety may be added to the sample.

In an embodiment, the second further moiety comprises a reference molecule having a substantially constant concentration in samples suspected to contain the target molecule in varying concentrations. This has the advantage that the second further moiety may be formed in situ by the formation of a binding couple including a labeled precursor of the second further moiety and the reference molecule.

In an embodiment, the sensor device is a magnetic sensor device, the label comprises a magnetic particle and the further label comprises a further magnetic particle. Magnetic sensor devices are particularly suitable for diagnostic use by other than trained professionals, as already has been explained.

In a preferred embodiment, the first moiety and the second moiety are attached to respective binding surfaces of a carrier, the sensor device further comprising a light source for emitting an input light beam into the carrier such that it is totally internally reflected in an investigation region at least one of said binding surfaces, the totally internally reflected light beam becoming frustrated resulting in a decrease of the totally internally reflected light intensity when the label and/or the further label are macroscopic scattering and/or absorbing magnetic particles; and a light detector for determining the amount of light in an output light beam that comprises at least some of the totally internally reflected light, said light detector being adapted to generate at least one of the first detection signal and the second detection signal.

Such a sensor device is capable of detection magnetic particles with high sensitivity and accuracy.

According to a further aspect, there is provided an apparatus comprising the sensor device of the present invention and a signal processor coupled to receive the second detection signal from the sensor device, said signal processor being adapted to determine a reference signal value from said second detection signal and to produce an output signal based on said reference signal value. The output signal may be presented to a user in visible or audible form, e.g. a reading on a display of the apparatus, and may simply be the reference signal value such that the user of the apparatus can compare this value with the expectation value of the reference signal to make an assessment of the reliability of a diagnostic finding produced with the apparatus.

Alternatively, the signal processor is further adapted to compare the reference signal value with an expectation value based on the expected amount of the second further moiety, wherein said output signal is based on said comparison. For instance, the output signal may be a pass/fail indication based on the comparison such that the user of the apparatus does not have to make this assessment himself. This reduces the risk of misinterpretation of the output signal.

In an embodiment, the reference signal value is a time-varying value based on the time-varying behavior of the second detection signal, which is typically a representation of the reaction kinetics of the binding reaction between the second moiety and the second further moiety. This information can for instance be used as calibration information, to which the signal processor may be further adapted to determine a correction factor from a difference between the expectation value and the reference signal value, determine a measurement value from the measurement signal; and determine a target molecule concentration from the product of the scaling factor and the measurement value, wherein said output signal comprises the determined target molecule concentration. This has the advantage that the deviation of the second detection signal value from its expectation value does not automatically lead to the rejection of the apparatus, thus avoiding or at least reducing the unnecessary rejection of such an apparatus.

In accordance with a yet further aspect of the present invention, there is provided a method of operating an apparatus of the present invention, the method comprising the generation of a first detection signal from the detection of the detectable label in the first further moiety bound to the first moiety, generating a second detection signal from the detection of the further detectable label in the second further moiety concentration bound to the second moiety, determining a reference signal value from said second detection signal; and producing an output signal based on said reference signal value, thereby facilitating a quality assessment of the sensor device.

In an embodiment, the method further comprises comparing the reference signal value with an expectation value; determining a correction factor from a difference between the expectation value and the reference signal value; generating the first detection signal; determining a measurement value from the first detection signal; and determining a target molecule concentration from the measurement value and the correction factor, wherein said output signal comprises the determined target molecule concentration. This avoids the unnecessary rejection of sensor devices, as previously explained.

In accordance with a further aspect of the present invention, there is provided a sample for use with a sensor device of the present invention, said sample comprising a first concentration of the first further moiety and a second concentration of the second further moiety, at least said second concentration being non-zero and known. Such a sample facilitates a failure analysis at the reference surface region.

BRIEF DESCRIPTION OF THE EMBODIMENTS

Embodiments of the invention are described in more detail and by way of non-limiting examples with reference to the accompanying drawings, wherein FIG. 1 schematically depicts a sandwich assay-based sensor device.

DETAILED DESCRIPTION OF THE DRAWINGS

It should be understood that the Figures are merely schematic and are not drawn to scale. It should also be understood that the same reference numerals are used throughout the Figures to indicate the same or similar parts.

In the present invention, "target molecule" may be any molecule of which concentration or presence as such is to be determined. Examples of target molecules are molecular targets such as proteins, enzymes, hormones, peptides, nucleic acids and cellular targets such as pathogen cells, bacterial cells and fungal cells. The target molecule may exist as such in a sample that is analyzed or may be formed in situ in a sensor device e.g. via a reaction that takes place in the device. If the sensor is used to monitor a reaction, the target may for example be the starting product of the reaction or a reaction product.

Where reference is made to "in solution" what is meant is that the reaction or assay is carried out in a liquid environment. The reagents that take part need not be dissolved in the fluid medium but may also be present in a suspended or dispersed state.

A selective binding is formed by the combination of two moieties (molecules), i.e. a moiety A and a further moiety B, with specific binding between the two moieties wherein the moiety binds to further moiety more strongly or preferentially than to other molecules and shows little or no cross reactivity with other molecules. In general, the affinity constant (Ka) for specific binding between moiety A and B is at least $10^6$ l/mol, more preferred at least $10^{10}$/mol, even more preferred at least $10^{11}$/mol, even more preferred at least $10^{12}$ l/mol, even more preferred from $10^{13}$ to $10^{17}$ l/mol.

The second further moiety D and the second moiety C which form the further selective binding of the reference sensor surface region may show little or no affinity for the target molecule, nor for the moieties A and B. In the context of the invention, "little or no affinity" is defined as having an affinity constant (Ka) of less than $10^3$ l/mol. If the second further moiety is also comprised in the first further moiety, e.g. the second further moiety is the secondary antibody of a sandwich assay and is also the antibody binding to the reference sensor, the second further moiety must be present in sufficient access such that its binding reaction to the target molecule is not affected by the competition with the binding to the second moiety at the reference sensor site and vice versa.

Various aspects and embodiments of the present invention will be described using a magnetic sensor device utilizing magnetic labels in the first and second further moieties. This is done by way of non-limiting example and for the sake of brevity only. It is reiterated that the principles of the present invention equally apply to assay-based sensor devices using different types of labels.

Figure 1:
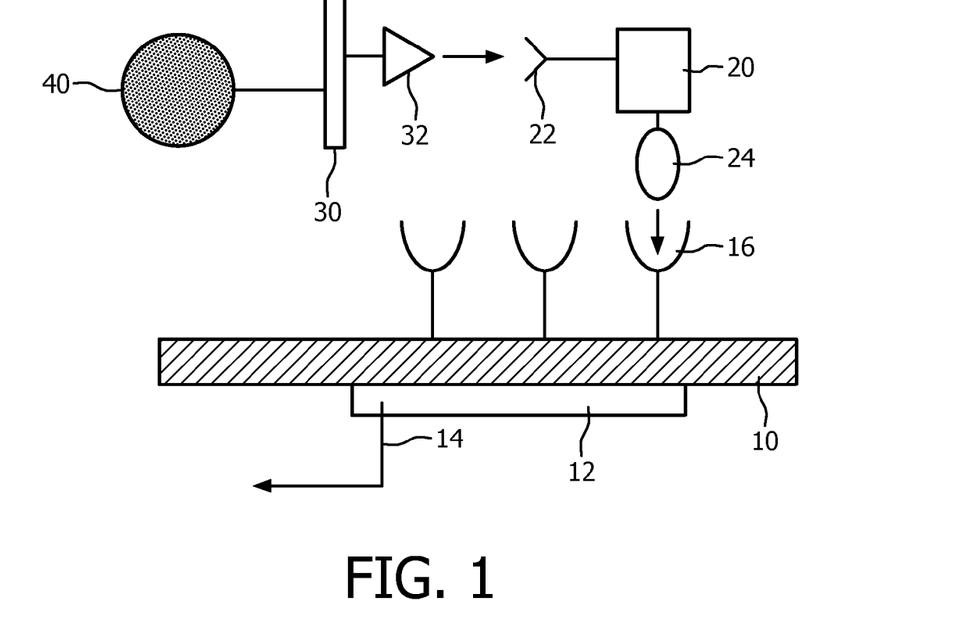

FIG. 1 schematically depicts a sensor device based on a sandwich assay. A first moiety 16 is attached to a region of a substrate surface 10 of the sensor device. The first moiety 16 is capable of specifically binding to the epitope 24 of the target molecule 20, which further comprises a further epitope 22, which is capable of forming another specific binding with an active site, e.g. a paratope on a further moiety precursor 30. The further moiety precursor 30 has been attached to a label 40, e.g. a magnetic particle. Any suitable way of attaching the further moiety 30 to the label 40, e.g. chemical binding including covalent, ionic, coordinative, electrostatic binding and so on may be used. The specific embodiment of this attachment is outside the scope of the present invention. A further moiety is formed when the epitope 22 and active site 32 are engaged, i.e. when the further moiety precursor 30 is attached to the target molecule 20. Upon binding of the further moiety to the first moiety 16, the presence of the label 40 on the sensor surface 10 can be detected by detector 12 by measuring an interaction of the label 40 with a generated stimulus. The stimulus generator has been omitted from FIG. 1 for reasons of clarity only. The intensity of the detection signal 14 is indicative of the amount of label 40 that has been attached to the surface 10 via the target molecule 20 such that the concentration of the target molecule 20 can be derived from the strength or intensity of the detection signal 14.

Figure 2:
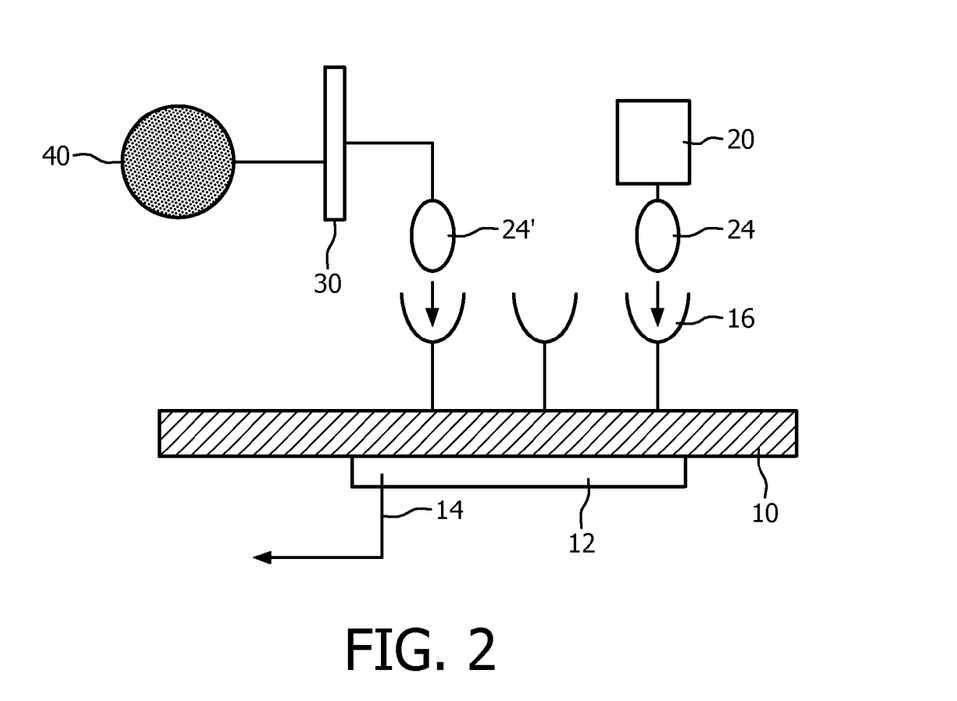
FIG. 2 schematically depicts a competitive assay-based sensor device.

FIG. 2 schematically depicts a sensor device based on a competitive assay. In this case, the target molecule 20 only comprises a single (suitable) epitope 24, which has to be used for binding the target molecule 20 to the first moiety, such that a further moiety 30' is provided that comprises an epitope 24' that is also capable of specifically binding to the first moiety 16. The further moiety 30', which may be a homologue of the target molecule 20, is attached to a label 40, e.g. a magnetic particle. The further moiety 30' competes with the target molecule 20 for the available binding sites provided by the first moiety 16 on the surface of the substrate 10. Again, the intensity of the detection signal 14 is indicative of the amount of label 40 that has been attached to the surface 10 via the target molecule 20. In this case, the concentration of the target molecule 20 is derived indirectly from the strength or intensity of the detection signal 14, because the intensity of this signal depends on the number of binding sites provided by the first moiety 16 that has been taken up by the first further moiety 30'.

The sandwich assay and competitive assay are non-limiting examples of assay types that may be used for the sensor device of the present invention. It is reiterated that any suitable assay type may be used.

The accurate operation of such assays is based on the reliance on reproducible reaction kinetics for the specific binding between the first moiety 16 and the epitope 22. For instance, the binding rate dN/dt for the sandwich assay of the sensor of FIG. 1 may be expressed as:

$$\frac{dN}{dt} = Ak_{on}[Cap][T]$$

wherein A is the area of the sensor surface (m$^2$), $k_{on}$ is the association constant of the binding reaction (m$^3$/s), [Cap] is the concentration of capture sites provided by the first moiety 16 on the sensor surface (m$^{-2}$) and T is the concentration of targets (m$^{-3}$) directly above the sensor surface.

Problems arise if, for whatever reason, the association reaction of this specific binding deviates from what is expected from this reaction rate. Examples of such reasons include:

The assay has not been fully completed;
Not enough fluid has been added to the test;
The actuation protocol of the assay has not been correctly followed;
No magnetic particles are present in the cartridge;
The dry reagents have not been properly dispersed;
Unusually high clustering of magnetic particles has occurred;
Extensive reagent degradation has occurred;
The disposable cartridge has not been properly stored (e.g. too high temperature or relative humidity) and integrated reagents have deteriorated over time.
The assay cartridge has been damaged, e.g. causing leakage of the fluid.

Although some of these problems may be detected visually, there is a significant risk that an untrained user of the assay-based sensor device will ignore such symptoms. Obviously, if no visible symptoms are present, it is very likely that an untrained user will simply use the faulty device and rely on its faulty readings.

Figure 3:
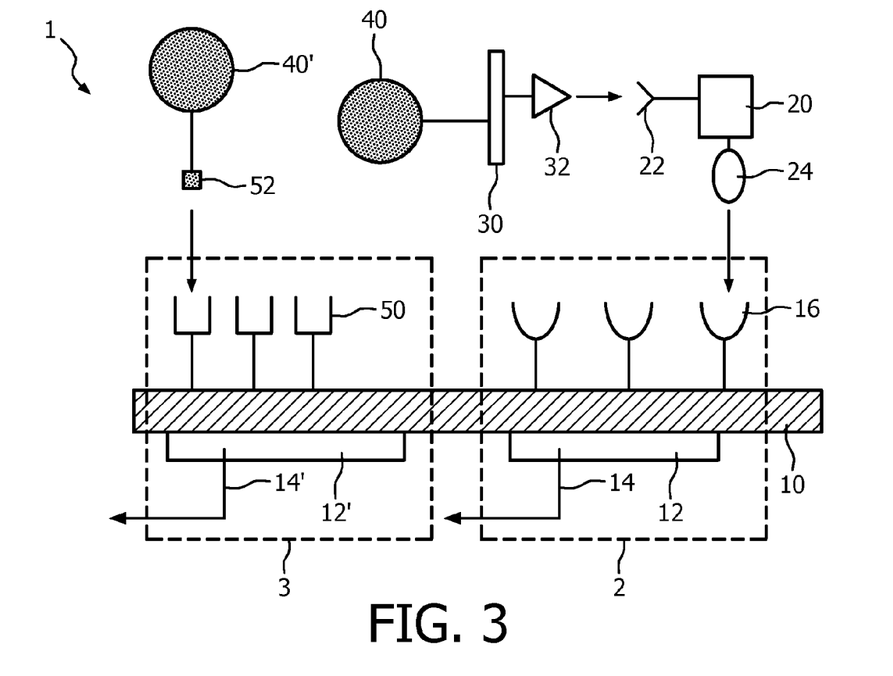
FIG. 3 schematically depicts an assay-based sensor device in accordance with an embodiment of the present invention.

In accordance with an embodiment of the present invention, there is provided a fail-safe assay-based sensor device 1 as shown in FIG. 3. The device 1 comprises a first sensor 2, which essentially is the same assay-based sensor as shown in FIG. 1. The first sensor 2 provides an assay for determining the presence of a moiety 20 in a sample such as a body fluid sample, e.g. saliva, sweat, urine or blood. The sensor 2 covers a predetermined area of a carrier 10, e.g. a substrate, of the sensor device 1. Upon formation of the specific binding between the epitope 24 and paratope 16, and epitope 22 and paratope 32 respectively, the magnetic particle 40 is anchored in the vicinity of the signal detection stage 12 such that upon generation of the stimulus, e.g. an electromagnetic field by a stimulus generator (not shown), the response to this stimulus induced by interaction between this stimulus and the magnetic particles 40 is detected by the signal detection stage 12.

As previously explained, the combination of the predetermined coverage of the substrate surface area and the density of the first further moiety 16 facilitates the correlation of e.g. the strength of the signal 14 generated by the signal determination stage 12 to the amount of the first moiety 20 that is attached to the substrate 10. In the context of the present invention, the term 'presence' is intended to cover both a binary measurement having a yes/no outcome as well as a measurement in which the concentration of the first moiety 20 in a sample is determined.

The sensor device 1 further comprises a second sensor 3 having a second moiety 50 covering a predetermined further area of the substrate 10 in a predetermined density. The second sensor 3 further comprises a further detection stage 12' for generating a reference detection signal 14'. The area covered by the second moiety 50 should not overlap with the area of the substrate 10 covered by the first moiety 16, at least not within the detection window of the first detection stage 12 and the second detection stage 12'. The second moiety 50 is capable of specifically binding to a second further moiety 52 that further comprises, e.g. is attached to, a magnetic particle 40'. The magnetic particle 40' may be the same size particle as magnetic particle 40, although this is not necessary. In an embodiment, the second further moiety 52 may also form a part of the first further moiety. For instance, the second further moiety may be identical to the first further moiety precursor 30. In this embodiment, the second further moiety 52 should be present in excess amounts at least during operation of the sensor device 1 such that the respective reaction rates of the binding reaction between the second further moiety 52 and the target molecule 20 on the one hand and the binding reaction between the second further moiety 52 and the second moiety 50 at the reference sensor site on the other hand are not affected by each other.

The concept of the present invention is based on the insight that when an assay-based reference sensor 3 for forming a specific binding with a labeled moiety, e.g. analyte being present in a known amount in the cartridge of the sensor device 1 or in a known concentration in a sample brought into the cartridge of the sensor device 1, the second signal detection stage 12' of the reference sensor 3 will generate a second detection signal 12' that has a strength or value falling within an expected signal value window when the formation of the specific binding formed by the second further moiety 52 to the second moiety 50 takes place as expected.

This is because the binding reactions in which suitable binding couples are formed have very stable binding rate constants as well as high affinity constants. For this reason, it is preferable that the specific binding has high stability, and that the moieties forming the specific binding can bind to each other at multiple or different regions, have good availability, and show low variability from batch to batch.

At this point it is noted that although sensor devices having multiple assays are known per se, none of these prior art devices teach the inclusion of a reference assay for determining a known amount, e.g. concentration, of a labeled moiety. Instead, the prior art devices teach the use of assays for the purpose of determining unknown amounts of analytes in samples.

It is further noted that the sensor device of the present invention is contemplated to be used for the measurement of stationary samples, which has the advantage over lateral flow sample devices that less sample volume is required. This for instance allows accurate measurement of target molecule presence in samples of no more than a few drops, e.g. blood samples collected by lancing a finger tip. This further allows for the actual measurement and the reference measurement to be performed in parallel contrary to the sequential measurements at multiple sites of a lateral flow sensor device, thus reducing the overall time required to complete a measurement.

The measurement sensor 2 and the reference sensor 3 may be located in different measurement chambers, with the labeled moiety 52 being present in the measurement chamber of the reference sensor 3 in a dried form. This relaxes the restrictions of the choice of the second further moiety 52, because in this embodiment a second further moiety 52 may be chosen that would interfere with the specific binding reaction at the measurement sensor region. Additionally, different assay buffers may be chosen to optimize each assay individually. It may be necessary to apply a separate reference fluid that is injected at the same time as the sample. It will be appreciated that in this case, the reference sensor provides useful information concerning material degradation but it is less suited to provide information concerning the correct addition of fluid to the measurement chamber because of the use of different fluids in the different chambers.

The respective sensor regions carrying the first moiety 16 and the second moiety 50 may be located on the same substrate 10 or on different substrates. This has the advantage that the labeled moiety cannot disturb the detection of the first detection stage 12 of measurement sensor 2, e.g. by aggregation of the magnetic particle 40' with the magnetic particle 40.

In an alternative embodiment, the reference assay, which acts as a fail-safe assay, is to be carried out in the same chamber as the measurement assay. To this end, a fail-safe assay may be chosen that does not interfere with the measurement assay, i.e. the epitope 24 of the first further moiety has no significant affinity for the second moiety 50 and the second further moiety 52 has no significant affinity for the first moiety 16.

It is important that the respective sensor regions comprising the first moiety 16 and the second moiety 50 have a comparable stability and robustness against environmental influences such that upon degradation of the first moiety 16, a deviation of the measurement signal 14' from its expectation value is also observed. For this reason, the robustness of the measurement sensor region comprising the first moiety 16 should be at least as good as the robustness of the measurement sensor region comprising the second moiety 50, e.g. an entity comprising a paratope for specifically binding to a further entity comprising a compatible epitope.

In an embodiment, a strong bonding couple may be used for the specific binding at the reference sensor 3. Non-limiting examples of suitable bonding couples include hapten-antibody pairs such as biotin-antibiotin, FITC-antiFITC and TexasRed-antiTexasRed, antibody-antiantibody pairs, in particular anti-antibodies that can bind to both the light and heavy chains on multiple regions of the antibody to improve the reproducibility and reaction rate of the binding reaction, and small molecule-protein pairs. A particularly preferable example of a small molecule-protein pair is avidin-biotin because of its polyvalent nature.

As previously mentioned, it is preferred that the second further moiety 52 including the magnetic particle 40' is present in the sensor device 1 in a dry form. This has the advantage that the wetting of the second further moiety 52 will depend on the amount of fluid in the sample entered into the sensor device 1. It is further preferable that the fail-safe assay of the reference sensor 3 is completed under the same conditions as the actual assay of the measurement sensor 2. This will be explained in more detail later.

Figure 4:
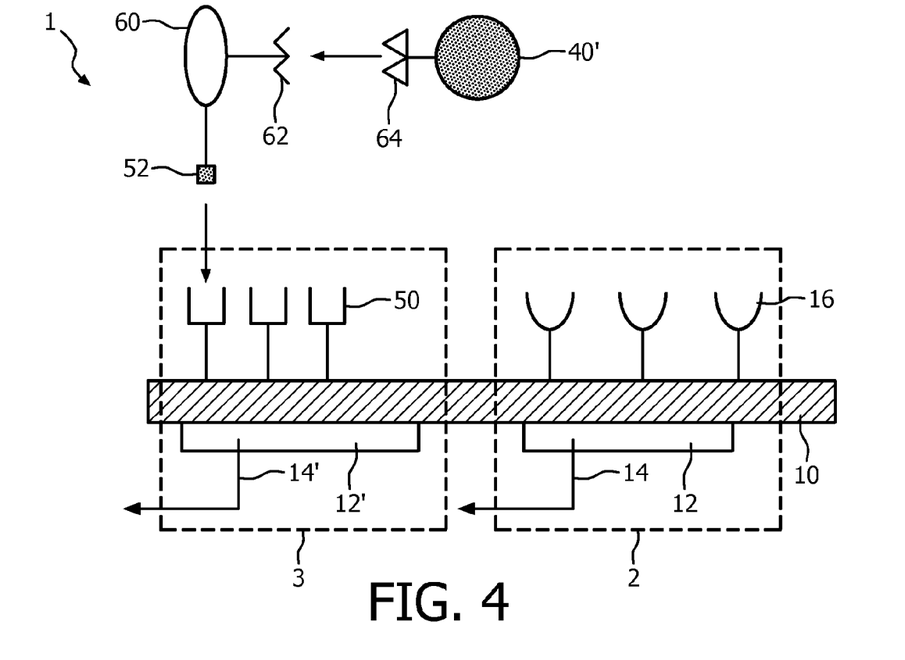
FIG. 4 schematically depicts an assay-based sensor device in accordance with an another embodiment of the present invention.

Any suitable assay type may be used for the reference sensor 3. In FIG. 3, the assay is formed by a direct specific binding reaction, in which no further biomolecule is required to anchor the magnetic particle 40' to the detection area of the sensor 3. Such an assay may be called a blank assay. FIG. 4 shows an alternative embodiment of a sensor device 1 of the present invention, in which the second further moiety forming one half of the specific binding pair of the assay of the reference sensor 3 is formed by the specific binding between the epitope 62 of a biomolecule 60 and the paratope 64 of the second further moiety precursor attached to the magnetic particle 40'. The biomolecule 60 further comprises an epitope 52 for specifically binding to the second moiety 50 on the detection area of the reference sensor 3. In other words, the assay of the reference sensor 3 is a sandwich assay in this non-limiting example. It is emphasized that only a part of the specific binding pairs of the assay of the measurement sensor 2 is shown in FIG. 4 for reasons of clarity only.

It is reiterated that any suitable type of assay may be used, such as the aforementioned sandwich assays and competitive assays, as well as inhibitive assays in which the target molecule does not bind to the sensor surface but instead inhibits the binding of the further moiety to the moiety on the sensor surface such that increasing concentrations of the target molecule lead to a reduction of the amount of further moiety (and label) binding to the sensor surface. In the case of an inhibitive assay, a predefined amount of the further moiety must be present to allow determination of the inhibited amount of the further moiety.

In case of a sandwich assay, or, in general, any type of assay in which the entity attached to the magnetic particle 40' is coupled to the detection region comprising the second moiety 50 through a biomolecule 60, it is important that both the concentrations of the biomolecule 60 and the entity comprising the magnetic particle 40' are known to produce a predictable detection signal 14'. This may for instance be achieved by selecting a biomolecule 60 that has a substantially constant concentration in samples in which the concentration of the analyte 20 typically varies. A non-limiting example of a suitable biomolecule 60 is serum albumin in blood samples, since the serum concentration in blood is usually substantially stable (unless the patient suffers from diseases affecting the serum composition).

Figure 5:
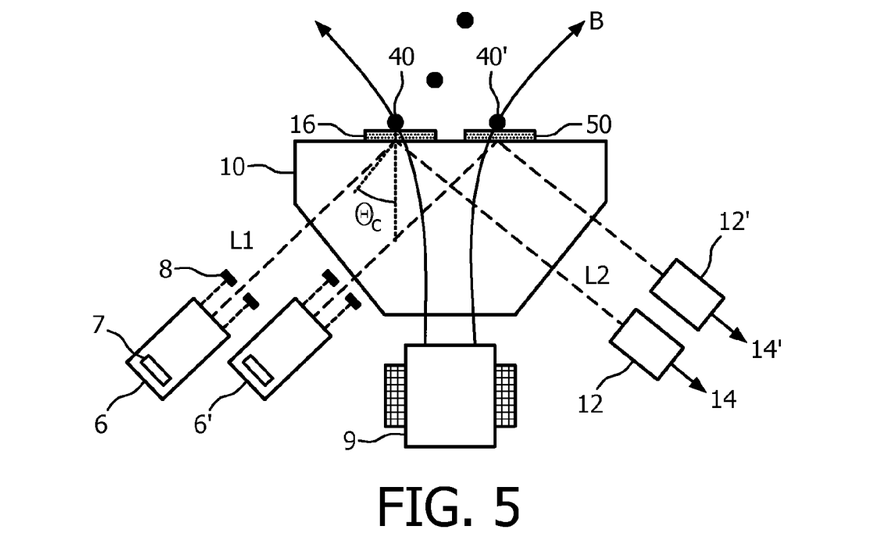
FIG. 5 schematically depicts a preferred embodiment of an assay-based sensor device.

FIG. 5 shows the general setup of a preferred sensor device. A central component of this device is the carrier 10 that may for example be made from glass or transparent plastic like polystyrene. The carrier 10 is located next to a sample chamber (not shown) in which a sample fluid with target components to be detected (e.g. drugs, antibodies, DNA, etc.) can be provided. The sample further comprises magnetic particles 40 and further magnetic particles 40' as previously explained, for example super-paramagnetic beads, as part of the respective moieties (not shown) that can specifically bind to the first moiety 16 and the second moiety 50 of the measurement sensor and the reference sensor respectively, as previously explained.

The sensor device comprises a magnetic field generator 9, for example an electromagnet with a coil and a core, for controllably generating a magnetic field B at the respective binding surfaces formed by the first moiety 16 and the second moiety 50. This magnetic field extends into the adjacent space of the sample chamber over these binding surfaces. The presence of magnetic field B allows for the manipulation of the magnetic particles 40 and 40', i.e. the magnetization and displacement of these particles in case magnetic fields with gradients are used. It is for example possible to attract magnetic particles 40, 40' to the binding surfaces of the measurement sensor and reference sensor in order to accelerate the binding of the associated target component to said surface.

The sensor device further comprises respective light sources 6 and 6', for each binding surface, which each for example may be a laser or an LED. Each light source generates an input light beam L1 which is transmitted into the carrier 10. The input light beam L1 arrives at its intended binding surface at an angle larger than the critical angle $\theta_c$ of total internal reflection (TIR) and is therefore totally internally reflected as an "output light beam" L2. The respective output light beams L2 leave the carrier 10 through another surface and are detected by respective light detectors 12 and 12', which for instance may be photodiodes. The light detectors 12 determine the amount of light of the incident output light beam L2 (e.g. expressed by the light intensity of this light beam in the whole spectrum or a certain part of the spectrum). The detector 12 is adapted to generate the first detection signal 14 and the detector 12' is adapted to generate the second detection signal 14'. The respective signals preferably are electrical signals, e.g. currents or voltages indicative of the aforementioned light intensity. The detection signals 14 and 14' may be forwarded to a signal processing unit (not shown) for evaluation.

In the respective light sources 6 and 6', a commercial DVD ($\lambda$=658 nm) laser-diode can be used. A collimator lens may be used to make the input light beam L1 parallel, and a pinhole 8 of e.g. 0.5 mm may be used to reduce the beam diameter. For accurate measurements, a highly stable light source is required. However, even with a perfectly stable power source, temperature changes in the laser can cause drifting and random changes in the output.

To address this issue, each light source 6 and 6' may optionally have an integrated input light monitoring sensor 7 for measuring the output level of the laser. The (low-pass filtered) output of the monitoring sensor 7 can then be coupled to a control unit (not shown), which may be the signal processor for processing the detection signals 14 and 14', which can divide the detection signal from a detector by the output of the corresponding sensor 7. For an improved signal-to-noise ratio, the resulting signal may be time-averaged. The division eliminates the effect of laser output fluctuations due to power variations, which has the advantage that no stabilized power source is needed, as well as temperature drift, which has the advantage that no precautions like Peltier elements are needed. Alternatively the output of sensor 7 can be used in a feedback control loop for the light source in order to keep its output as measured by the sensor 7 stable over time.

A further improvement can be achieved if not (or not only) the laser output itself is measured, but the final output of the respective light sources 6 and 6'. As FIG. 1 coarsely illustrates, only a fraction of the light output exits the pinhole 8. Only this fraction will be used for the actual measurement in the carrier 10, and is therefore the most direct source signal. Obviously, this fraction is related to the output of the light source, as determined by e.g. the integrated sensor 7, but will be affected by any mechanical change or instability in the light path; a laser beam profile is approximately elliptical with a Gaussian profile, i.e. quite non-uniform. Thus, it is advantageous to measure the amount of light of the input light beam L1 after each pinhole 8 and/or after eventual other optical components of the respective light sources 6 and 6'. This can be done in a number of ways, for example:

a parallel glass plate (not shown) can be placed under 45° to the light beam L1 or a beam splitter cube (e.g. 90% transmission, 10% reflection) can be inserted into the light path L1 behind each pinhole 8 to deflect a small fraction of the light beam towards a separate input-light monitoring sensor (not shown);

a small mirror at the edge of each pinhole 8 or the input light beam L1 can be used to deflect a small part of the beam towards a detector (not shown).

In FIG. 5, separate light sources 6 and 6' are shown by way of non-limiting example. Alternative embodiments, such as an embodiment in which a single light source 6 is used, which location of may be configurable to switch its interaction between the carrier area comprising first moiety 16 and the carrier area comprising second moiety 50 are equally feasible. In a further alternative embodiment, a single light source 6 is used to illuminate both sensor areas simultaneously. Other design variations will be apparent to the skilled person.

The sensor device described in FIG. 5 applies optical means for the detection of magnetic particles 40, 40' and the target components for which detection is actually of interest. For eliminating or at least minimizing the influence of background (e.g. of the sample fluid, such as saliva, blood, etc.), the detection technique preferably is surface-specific. This is achieved by using the principle of frustrated total internal reflection which is explained in the following.

According to Snell's law of refraction, the angles $\theta_A$ and $\theta_B$ with respect to the normal of an interface between two media A and B satisfy the equation:

$$n_A \sin \theta_A = n_B \sin \theta_B$$

with $n_A$, $n_B$ being the refractive indices in medium A and B, respectively. A ray of light in a medium A with high refractive index (e.g. glass with $n_A$=2) will for example refract away from the normal under an angle $\theta_B$ at the interface with a medium B with lower refractive index such as air ($n_B$=1) or water ($n_B \approx 1.3$). A part of the incident light will be reflected at the interface, with the same angle as the angle $\theta_A$ of incidence. When the angle $\theta_A$ of incidence is gradually increased, the angle $\theta_B$ of refraction will increase until it reaches 90°. The corresponding angle of incidence is called the critical angle, $\theta_c$, and is given by $\sin \theta_c = n_B/n_A$. At larger angles of incidence, all light will be reflected inside medium A (glass), hence the name "total internal reflection". However, very close to the interface between medium A (glass) and medium B (air or water), an evanescent wave is formed in medium B, which decays exponentially away from the surface. The field amplitude as function of the distance z from the surface can be expressed as:

$$\exp(-k\sqrt{n_A^2 \sin^2(\theta_A) - n_B^2} \cdot z)$$

with $k=2\pi/\lambda$, $\theta_A$ being the incident angle of the totally reflected beam, and $n_A$ and $n_B$ the refractive indices of the respective associated media.

For a typical value of the wavelength $\lambda$, e.g. $\lambda$=650 nm, and $n_A$=1.53 and $n_B$=1.33, the field amplitude has declined to $\exp(-1) \approx 0.37$ of its original value after a distance z of about 228 nm. When this evanescent wave interacts with another medium like the magnetic particles 40, 42 in the setup of FIG. 5, part of the incident light will be coupled into the sample fluid. This is called "frustrated total internal reflection", and the reflected intensity will be reduced while the reflected intensity will be 100% for a clean interface and no interaction. Depending on the amount of disturbance, i.e. the amount of magnetic beads 40, 40' on or very near, e.g. within about 200 nm, to the binding surface 12, the reflected intensity will drop accordingly. This intensity drop is a direct measure of the amount of bonded magnetic beads 40, 40', and therefore of the concentration of target molecules.

When the mentioned interaction distance of the evanescent wave of about 200 nm is compared with the typical dimensions of anti-bodies, target molecules and magnetic beads, it is clear that the influence of the background will be minimal. Larger wavelengths $\lambda$ will increase the interaction distance, but the influence of the background liquid will still be very small.

For the materials of a typical application, medium A of the carrier 10 can be glass and/or some transparent plastic with a typical refractive index close to 1.52. Medium B in the sample chamber will usually be water-based and have a refractive index close to 1.3. This corresponds to a critical angle $\theta_c$ of 60°. An angle of incidence of 70° is therefore a practical choice to allow fluid media with a somewhat larger refractive index (assuming $n_A$=1.52, $n_B$ is allowed up to a maximum of 1.43). Higher values of $n_B$ would require a larger $n_A$ and/or larger angles of incidence. Further embodiments of such a sensor device can be found in published international application WO2008/072156 which is hereby enclosed by reference in its entirety.

Figure 6:
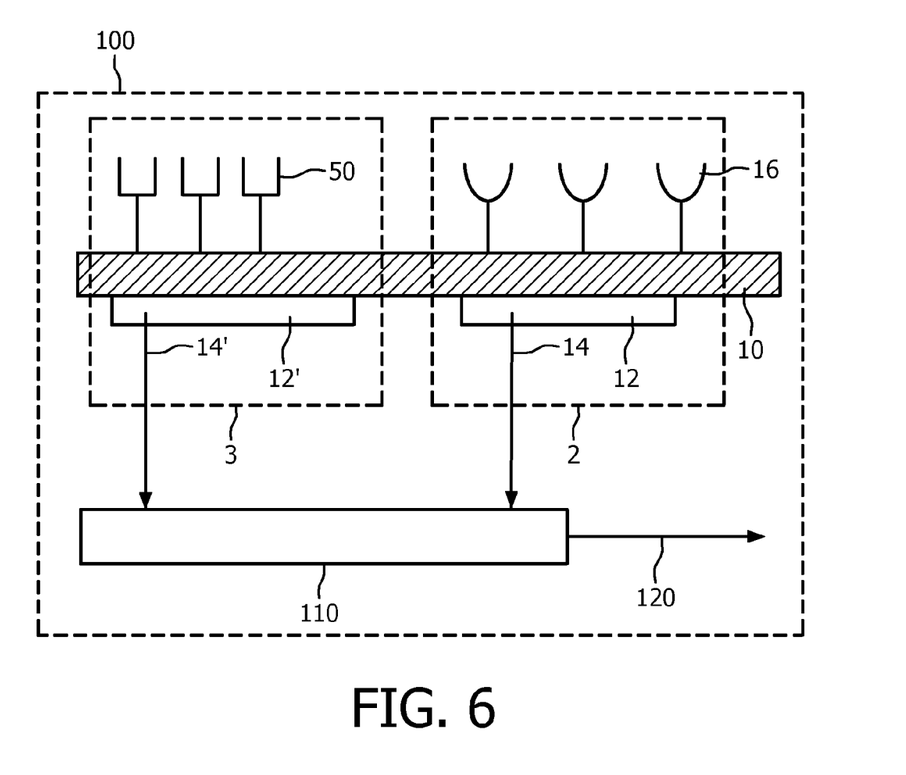
FIG. 6 schematically depicts an apparatus in accordance with an embodiment of the present invention.

FIG. 6 shows an example embodiment of an apparatus 100 comprising an embodiment of a sensor device 1 of the present invention. The apparatus comprises a signal processing stage 110 for processing the measurement detection signal 14 and the reference detection signal 14'. The signal processing stage 110 may be arranged to process analog or digital detection signals. Also, the processing stage 110 may be implemented by a single processor for processing both the measurement detection signal 14 and the reference detection signal 14, or by different processors each dedicated to process one of these signals. The processing stage 110 may be implemented as a multi-functional processing unit, in which the signal processing instructions for processing the measurement detection signal 14 and the reference detection signal 14 are implemented in software. Alternatively, these signal processing instructions may be hard-coded into the processing stage 110. The processing stage 110 may be provided on the same substrate 10 as the measurement sensor 2 and the measurement sensor 3 or may be provided on a different substrate, with the different substrates being mounted on the same carrier, e.g. a printed circuit board, or on different carriers. Other embodiments will be apparent to the skilled person.

In an embodiment, the signal processing stage 110 is arranged to compare the reference detection signal 14' of the reference sensor 3 with an expectation value of the reference detection signal 14'. The expectation value essentially is the value that the reference detection signal 14' should comprise if the specific binding of the assay of the reference sensor 3 is formed as expected e.g. from the known amount of the second further moiety, e.g. the moiety comprising epitope 52, the known reaction rate of the specific binding reaction, the detection area covered by the second moiety comprising the paratope 50 and the density of the second moiety in the detection area. This expectation value may be stored in any suitable storage device (not shown) that is accessible by the signal processing stage 110. In case of the second further moiety 52 is present in excess amounts during the measurement, it will be apparent that the expectation value corresponds to the signal value obtained when substantially all binding sites of the reference sensor have specifically bound to the second further moiety 52.

Figure 7:
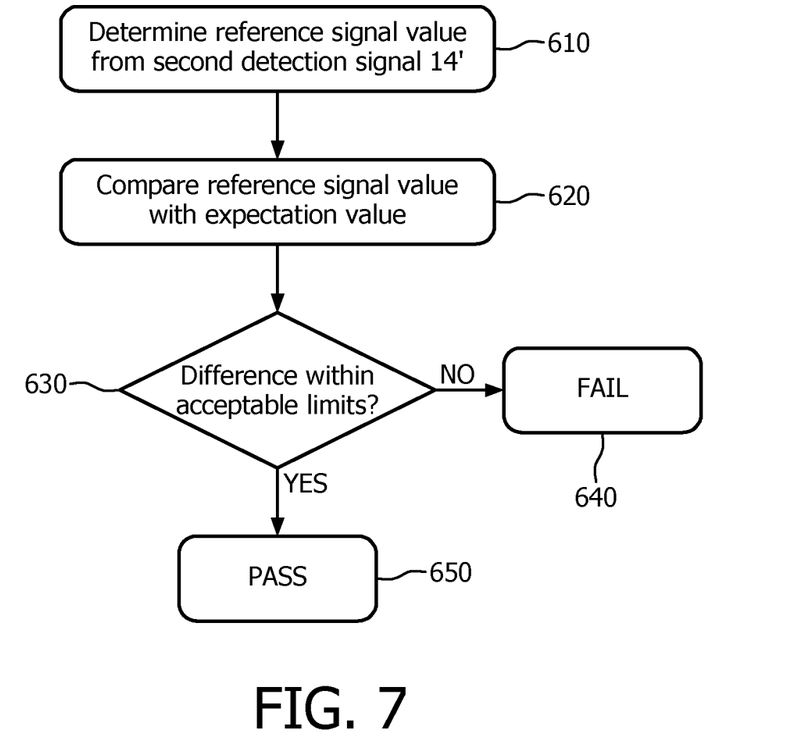
FIG. 7 depicts a flow chart of an aspect of a method in accordance with an embodiment of the present invention.

An embodiment of a processing method implemented by the signal processing stage 110 is shown in FIG. 7. In step 610, the value of reference signal 14' is determined and compared with its expectation value in step 620. In step 630, it is determined if the difference between the value of the reference signal 14' and its expectation value falls within acceptable limits. These limits may be seen as the expected signal value window in which the detected reference signal 14' falls when the binding reaction of the second further moiety to the second moiety has taken place as expected, thus indicating a correctly functioning sensor device 1 and a correctly prepared sample for determining the presence of the analyte of interest 20. In case the value of the detected reference signal 14' falls outside the expected signal value window, an indication is generated in step 640 signaling that the sensor device 1 is unreliable such that the user is informed to ignore the measurement result of measurement sensor 2. Alternatively, the signal processing stage 110 may block the measurement result being made available to the user to avoid the risk that the failure warning is ignored and the unreliable measurement is being used for diagnostic purposes anyway. If it is determined in step 630 that the value of the detected reference signal 14' falls within the expected signal value window, it is established that the measurement performed with the assay of the measurement sensor 2 is reliable, and an indication to this effect is generated in step 650. This simply may be the provision of the measurement result, or preferably, includes an indication of the sensor device 1 passing the fail-safe test.

The signal processing stage 110 may be configured to generate an output signal 120 that is indicative of the outcome of the fail-safe test, such as a signal to be converted into an audible signal by e.g. a loudspeaker (not shown) or a signal to be converted into an visible signal by e.g. a display (not shown). Other suitable ways of informing a user of the apparatus of the reliability of the findings of the sensor device 1 will be immediately apparent to the skilled person.

In an alternative embodiment, the signal processing stage 110 is arranged to generate a calibration signal for calibrating the measurement detection signal 14 on the basis of the deviation of the deviation of the reference detection signal 14' from its expectation value. This for instance may be applicable when evaluating the time-dependent evolution of the reference detection signal 14', where it may be apparent from the shape of the transient that the specific binding reaction has exhibited the expected reaction kinetics but at deviating signal intensity.

Figure 8:
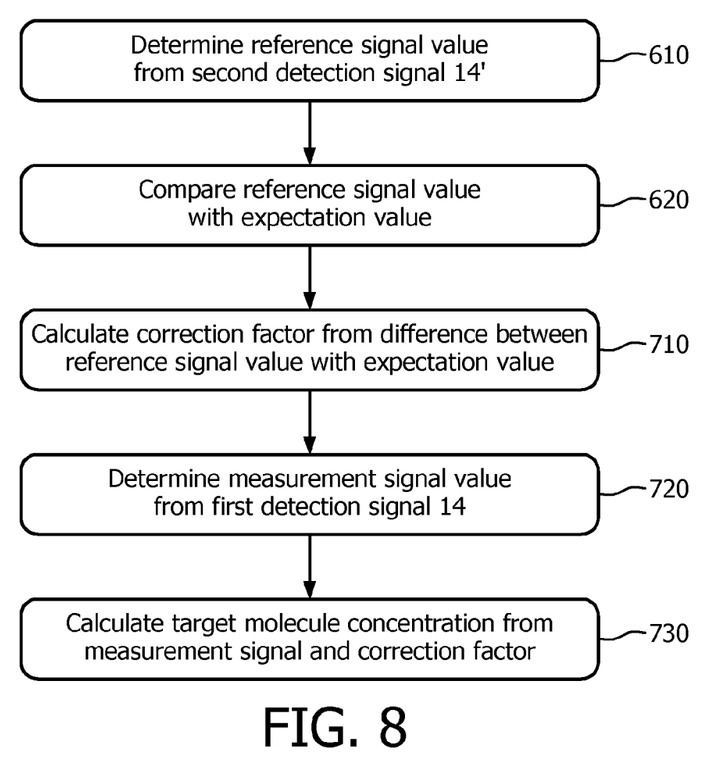
FIG. 8 depicts a flow chart of another aspect of a method in accordance with an embodiment of the present invention.

An example embodiment of such a processing method is shown in FIG. 8, where after the steps 610 and 620 as previously discussed, a correction factor is calculated in step 710 from the difference between the actual value of the reference detection signal 14' and its expectation value, after which the value of the measurement detection signal 14 from the measurement sensor 2 is determined in step 720 followed by the determination of the concentration of the analyte 20 in the sample in step 730 using the determined measurement signal value and the correction factor. Obviously, step 720 may be executed at any suitable time, e.g. in parallel with any of steps 610, 620 and 710.

It is pointed out that in the context of the present invention, the phrase 'expectation value' also covers a plurality of values defining the time-dependent evolution of the reference detection signal 14'. In fact, the time-dependent evolution of the reference detection signal 14' can provide useful information about different potential problems with the assays of the sensor device 1, as will be explained with the aid of FIG. 9, in which a typical curve of the evolution of the reference detection signal 14' as a function of time is depicted for a reference assay comprising a biotin-bovine serum albumin (BSA) moiety immobilized on the surface of the reference sensor 3, and magnetic particles 40' attached to anti-biotin.

Figure 9:
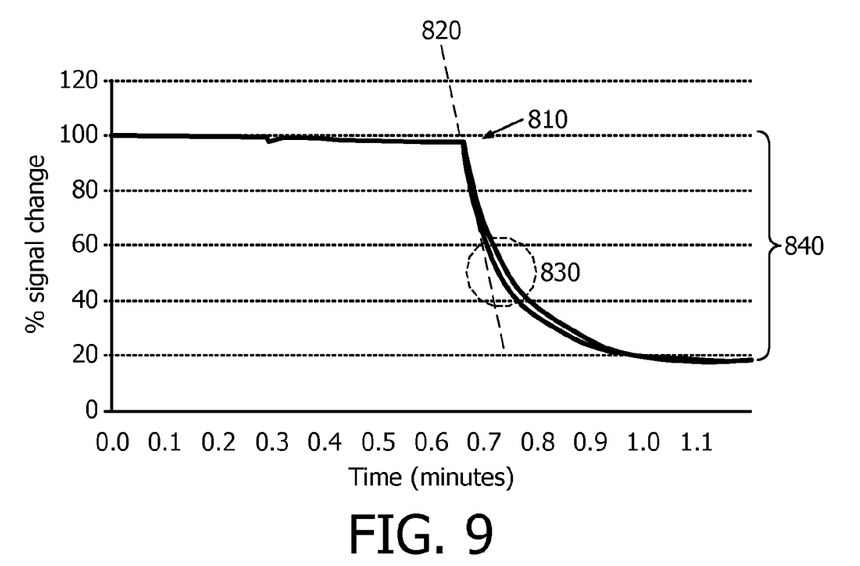
FIG. 9 depicts a reference signal obtained from an assay-based magnetic sensor device in accordance with an embodiment of the present invention.

This signal curve can be interpreted to give valuable information about the following potential problems:

- sample preparation, and in particular the preincubation/mixing step of the sample. If the signal part 810 shows an unusually large change in signal intensity during this preparation phase, this is an indication that magnetic particles have clustered, thereby forming sedimentation in the detection area of the reference sensor 3.
- The maximum signal 850 after the binding couple formation step provides information about particle concentration and sample viscosity. This facilitates the detection of incomplete redispersion of particles, cartridge leakage, absence of magnetic particles in the test, incorrect test liquids and so on.
- The difference 830 between the maximum and minimum amplitude of the reference detection signal 14' provides information about particle concentration and monodispersity of the magnetic particles 40' influencing the detection signal 14'. The amplitude of the modulation scales with the number of mono-disperse particles in solution. This signal can therefore be used to check for various failure mechanism that may influence the measurement signal. If during manufacturing to many beads were added to the cartridge this would increase the modulation amplitude of the signal. When some of the particles do not dissolve correctly this will lead to a lower modulation amplitude. Clustering of the beads can also be detected, since this will reduce the modulation amplitude because clusters cannot move as freely as single beads.
- The slope 820 of the binding reaction in which the strong binding couple of the reference sensor 3 is formed provides information about functionality of assay. Since the measurements typically take place in the kinetic regime, the slope is proportional to the number of bindings as a function of time which is proportional to the association constant which is a measure of the functionality of the assay.
- The maximum signal change 840 provides information about particle concentration and the effectiveness of the specific binding reaction. The latter provides information about the biological integrity of the sensor device 1.
- After the binding reaction is completed, or after a fixed amount of time, whatever is appropriate, the sensors 2 and 3 are washed to remove unbound magnetic particles 40, 40' such that the measurement detection signal 14 and the reference detection signal 14' are affected by magnetic particles that are bound to the respective detection regions only. The signal after washing provides absolute information about whether the reference assay is fully functional, e.g. is indicative of non-redispersion, cartridge damage leading to leakage, wrong sample type, insufficient volume, substantial biological degradation and so on. Also, substantial temperature variations during test will yield a reference detection signal 14' after washing that differs significantly from its expectation value because the reaction rate of the binding reaction is temperature-dependent.

Finally, for a measurement performed with the sensor device 1 to be reliable, all parts of the signal curve must be present. This is an indication that the correct actuation protocol has been used and completed.

It is preferable that the sensor device comprises a magnetic field generator for attracting the magnetic particles to the sensor surface to facilitate detection of the various parts of this curve. Upon application of the magnetic field, the behavior of the magnetic particles in this field can be evaluated. This evaluation may also be used as a reference. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sensor device for detecting the presence of a target molecule in a stationary sample, the sensor device comprising:
   a measurement sensor including a first moiety including a measurement region of a substrate including a first moiety, which is a paratope, which selectively binds to an epitope of the target molecule including a further epitope, which can bind with a paratope present on a first further moiety comprising a detectable label, wherein an amount of the first further moiety binding to the first moiety is related to an amount of the target molecule present in said sample, the measurement sensor being configured to generate a first detection signal in response to detection of the detectable label in the first further moiety bound to the first moiety; and
   a reference sensor including a reference region of the substrate including a second moiety which selectively binds to a second further moiety including a further detectable label, the reference sensor being configured to generate a second detection signal in response to detection of the further detectable label in the second further moiety bound to the second moiety;
   a signal processor configured to:
   during operation of the sensor device, determine whether the second detection signal falls within a signal value window corresponding to a predefined amount of the second further moiety binding to the second moiety; and
   in response to the second detection signal falling outside the signal value window, generating a failure signal indicative of any of completion failure of the assay, insufficient fluid added to the test, incorrect preparation of the actuation protocol of the assay, lack of magnetic particles in the cartridge, failure of dry agents to disperse, unusually high clusters of magnetic particles, extensive reagent degradation, integrated reagent deterioration, or a damaged assay cartridge; and
   a speaker or display which issues an audible or visible output in response to the failure signal.

2. The sensor device of claim 1, wherein the detectable label of the first moiety and the further detectable label of the second moiety are the same, and wherein the second further moiety is also comprised in the first further moiety.

3. The sensor device of claim 1, wherein the first further moiety has no significant affinity for the second moiety and the second further moiety has no significant affinity for the first moiety.

4. The sensor device of claim 1, wherein the measurement sensor is located in a first measurement chamber and the reference sensor is located in a second measurement chamber.

5. The sensor device of claim 1, wherein the second further moiety is in a dried form and wherein a known amount of the second further moiety is added to the sample.

6. The sensor device of claim 1, wherein the second moiety and the second further moiety are selected from the group of hapten-antibody pairs including biotin-antibiotin, fluorescinisothiocyanate-anti fluorescinisothiocyanate and Texas Red-antiTexas Red; antibody-antiantibody pairs and small molecule-protein pairs;
   wherein the anti-antibodies can bind to both light and heavy chains on multiple regions of the antibody.

7. The sensor device of claim 1, wherein the second further moiety further includes a reference molecule having a substantially constant concentration in samples that contain the target molecule in varying concentrations.

8. The sensor device of claim 1, wherein the sensor device is a magnetic sensor device and the label includes a magnetic particle and the further label includes a further magnetic particle, and wherein the magnetic sensor device includes a magnetic field generator for attracting the magnetic particle and the further magnetic particle to the respective sensors.

9. The sensor device of claim 8, wherein the first moiety and the second moiety are attached to respective binding surfaces of a carrier, the sensor device further comprising:
   a light source configured to emit an input light beam into the carrier which arrives at least at one of the binding surfaces at an angle larger than a critical angle of total internal reflection such that the light beam is totally internally reflected as output light beams leaving the carrier through another surface and, in response to the totally internally reflected light beam becoming frustrated, an intensity of the totally internally reflected light decreases in response to the label and/or the further label macroscopically scattering and/or absorbing the magnetic particles; and
   a light detector for determining an amount of light in an output light beam that includes at least some of the frustrated totally internally reflected light, said light detector being configured to generate at least one of the first detection signal and the second detection signal.

10. The apparatus of claim 1, wherein a reference signal value derived from the second detection signal is a time-varying value based on a time-varying behavior of the second detection signal.

11. The apparatus of claim 10, wherein:
- the signal processor stage is further configured to compare the reference signal value with an expectation value based on the expected amount of the second further moiety; and
- said failure signal is based on said comparison.

12. The apparatus of claim 11, wherein the signal processor stage is further configured to:
- determine a correction factor from a difference between the expectation value and the reference signal value;
- determine a measurement value from the first detection signal; and
- determine a target molecule concentration from the correction factor and the measurement value.

\* \* \* \* \*